United States Patent
Bonda et al.

(10) Patent No.: US 7,915,330 B2
(45) Date of Patent: Mar. 29, 2011

(54) PHOTOSTABILIZING SILICONE FLUIDS

(75) Inventors: Craig A. Bonda, Winfield, IL (US); Anna Pavlovic, Elmwood Park, IL (US); Anthony J. O'Lenick, Jr., Dacula, GA (US)

(73) Assignee: Hallstar Innovations Corp., Chicago, IL (US)

( * ) Notice: Subject to any disclaimer, the term of this patent is extended or adjusted under 35 U.S.C. 154(b) by 330 days.

(21) Appl. No.: 12/205,546

(22) Filed: Sep. 5, 2008

(65) Prior Publication Data

US 2009/0069466 A1    Mar. 12, 2009

Related U.S. Application Data

(60) Provisional application No. 60/935,917, filed on Sep. 6, 2007.

(51) Int. Cl.
| | |
|---|---|
| C08K 5/00 | (2006.01) |
| C08K 5/34 | (2006.01) |
| C08K 5/3445 | (2006.01) |
| C08K 5/15 | (2006.01) |
| C08C 1/14 | (2006.01) |
| B32B 7/12 | (2006.01) |
| B60C 1/00 | (2006.01) |
| C08G 73/10 | (2006.01) |
| C08G 77/00 | (2006.01) |
| C08L 75/00 | (2006.01) |
| C07F 7/10 | (2006.01) |
| A61K 8/00 | (2006.01) |

(52) U.S. Cl. .......... 524/87; 524/100; 524/106; 524/110; 524/160; 524/186; 524/287; 524/291; 524/359; 524/588; 528/41; 528/43; 556/416; 556/417; 556/415; 424/60; 424/47; 424/70.12; 525/474; 525/479; 560/60

(58) Field of Classification Search .............. 524/87, 524/100, 106, 110, 160, 186, 287, 291, 359, 524/588; 528/41, 43; 556/416, 417, 415; 424/60, 47, 70.12; 525/474, 479; 560/60
See application file for complete search history.

(56) References Cited

U.S. PATENT DOCUMENTS 3,715,334 A    2/1973   Karstedt
(Continued)

FOREIGN PATENT DOCUMENTS

SU    1273360    11/1986

OTHER PUBLICATIONS

Senchenya, N. G., et al. "Silicon-containing esters of α-cyanoacrylic acid: synthesis and properties" Russian Chem. Bul., vol. 42(5), pp. 909-911 (1993).

*Primary Examiner* — William K Cheung
(74) *Attorney, Agent, or Firm* — Marshall, Gerstein & Borun LLP

(57) ABSTRACT

A silicone fluid comprising a chromophore-substituted polyorganosiloxane having a formula (2):

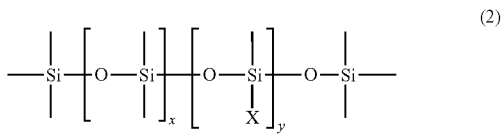

wherein x is an integer in the range of 60 to 2000; y is an integer in the range of 5 to 100; a ratio x:y is in a range of about 10:1 to about 20:1; and X is a photostabilizing chromophore.

22 Claims, 1 Drawing Sheet

U.S. PATENT DOCUMENTS

| | | |
|---|---|---|
| 4,307,240 A | 12/1981 | Ching |
| 4,562,278 A | 12/1985 | Hill |
| 4,804,531 A | 2/1989 | Grollier |
| 5,306,485 A | 4/1994 | Robinson et al. |
| 5,827,509 A * | 10/1998 | Richard et al. ............... 424/60 |
| 6,277,892 B1 | 8/2001 | Deckner et al. |
| 6,492,326 B1 | 12/2002 | Robinson et al. |
| 6,841,649 B1 | 1/2005 | O'Lenick, Jr. |
| 2004/0180020 A1 | 9/2004 | Manelski et al. |
| 2005/0142095 A1 | 6/2005 | Scancarella et al. |

* cited by examiner

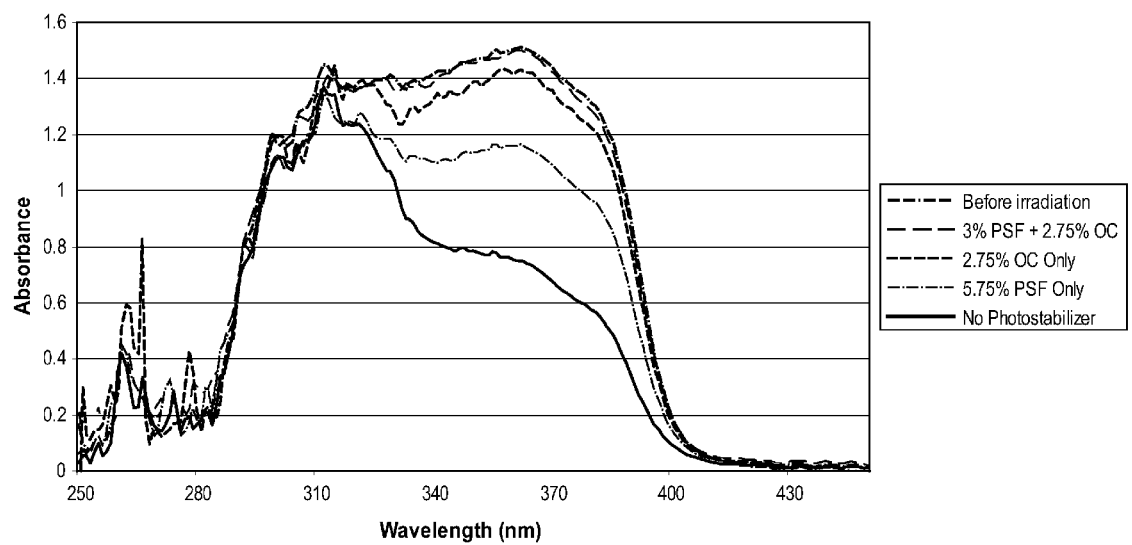

PHOTOSTABILIZING SILICONE FLUIDS

CROSS-REFERENCE TO RELATED APPLICATION

The present application claims the benefit of priority of U.S. Provisional Patent Application No. 60/935,917 filed on Sep. 6, 2007. The entire text of the priority application is incorporated herein by reference in its entirety.

BACKGROUND OF THE INVENTION

1. Field of the Disclosure

The disclosure generally relates to silicone polymer fluids and silicone polymer fluid-containing compositions for sunscreening and photoprotection. More specifically, to silicone polymers containing pendant α-cyano-β,β-diphenylacrylate derivatives for the photostabilization of photoprotective (UV-absorbing) compounds.

2. Brief Description of Related Technology

Ultraviolet radiation (light) can cause various types of chronic and acute damage to human skin. Overexposure to ultraviolet light having a wavelength from about 280 nm or 290 nm to about 320 nm (UV-B) can produce sunburn, while chronic overexposure can lead to skin cancer and weakening of the immune system. UV-B radiation is capable of causing damage to DNA by chemically altering the DNA structure. Both UV-A radiation (about 320 nm to about 400 nm) and UV-B radiation can damage collagen fibers and vitamin A in the skin, leading to a reduction of skin elasticity and accelerated aging of the skin.

Additionally, ultraviolet radiation from the sun or artificial sources can damage coatings containing photoactive substances, such as photoactive pigments and dyes, by altering chemical bonds in the structure of a component, such as a polymer, a pigment, or a dye. This photodegradation can lead to color fading, loss of gloss, and loss of physical and protective properties of a coating.

The inclusion of UV-absorbing and photoprotective compounds in compositions such as sunscreens and coatings can serve to reducing the damaging effects of UV radiation. These photoprotective compounds are often chromophore-containing organic molecules but themselves are prone to photodegradation and, thereafter, can absorb little or no additional UV light. The photostabilization of these photoprotective molecules require the molecules to return to the ground state faster than the photodegradation occurs. There are known photostabilizing sunscreen additives, e.g. octocrylene, that quench the photoexcited state of sunscreening molecules. For example, octocrylene is known to photostabilize avobenzone.

The photostabilization of cosmetic sunscreen compositions containing dibenzoylmethane derivatives, e.g., avobenzone, requires at least 1% by weight of an α-cyano-β,β-diphenylacrylate, e.g., octocrylene, and a 4:5 mole ratio of the α-cyano-β,β-diphenylacrylate to the dibenzoylmethane derivative. Obviously, increasing the weight percentage of the photoprotective molecule in the composition requires an increase in the weight percentage of the photostabilizing molecule, but these increases can lead to degradation of cosmetic, and/or structural properties of compositions containing the molecules.

While octocrylene can photostabilize, to some degree, dibenzoylmethane derivatives, there still exists a need in the photoactive composition art to find one or more compounds that photostabilize photoactive materials. Moreover, enhanced photostabilizing compounds are needed for material and dermatologic protection.

Quite surprisingly, it has been found that silicon polymers containing α-cyano-β,β-diphenylacrylate groups, preferably alkoxy-substituted α-cyano-β,β-diphenylacrylate groups efficiently photostabilize UV-absorbing organic molecules even at low loadings compared to the quantity of UV-absorbing compounds. Additionally, the disclosed silicone fluids enhance the photoprotection provided by UV-absorbing organic molecules thereby lessening the required loading necessary to provide sufficient UV protection.

SUMMARY OF THE INVENTION

Disclosed herein are silicone fluids and compositions thereof that enhance the photoprotection provided by and photostability of photodegradable UV-absorbing compounds.

One aspect of the compositions and methods described herein is to provide a method of decreasing the photodegradation of a UV-absorbing compound or photodegradable polymer by the addition thereto of an effective amount, e.g., 0.05% to 25%, based on the weight of the photodegradable UV-absorbing compound or photodegradable polymer, preferably 0.1 to 10%, of a compound of formula (I).

Another aspect of the compositions and methods described herein is to provide a method for photostabilizing a photodegradable UV-absorbing compound or photodegradable polymer that includes a photoprotective compound, such as a dibenzoylmethane derivative, by the addition of a compound of formula (I).

Yet, another aspect of the compositions and methods described herein is to provide a method for photostabilizing a photodegradable UV-absorbing compound or photodegradable polymer that does not include a photoprotective compound, such as a dibenzoylmethane derivative, by the addition of compound of formula (I).

Still another aspect of the compositions and methods described herein is to provide a method for enhancing the photostability of a photodegradable UV-absorbing compound or photodegradable polymer that includes a phostostabilizing compound, e.g., octocrylene, through synergistic effects by the addition of compound of formula (I).

Additional features of the compositions and methods described herein may become apparent to those skilled in the art from a review of the following detailed description, taken in conjunction with the drawings, the examples, and the appended claims.

BRIEF DESCRIPTION OF THE DRAWING

For a more complete understanding of the disclosure, reference should be made to the following detailed description and accompanying drawing wherein:

The drawing is a comparison of sunscreen formulations prior to and post exposure to irradiation, showing the UV absorbance of the sunscreen formulation, the decrease in UV absorbance upon irradiation and the photoprotective and photostabilizing effects of silicone fluids on the sunscreen formulation. Remarkably, the synergistic photostability provided by the mixture of silicon fluid and octocrylene was nearly 100%.

While the disclosed silicone fluids are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The invention generally relates to photoprotective and photostabilizing silicone fluids and compositions thereof. The silicone fluids described herein contain photostabilizing chromophores attached to silicone polymers. Compositions including the silicone fluids, together with another UV-absorbing, photodegradable compound, have enhanced photostability and provide prolonged photoprotection.

The silicone fluids described herein can be prepared by attaching one or more particular photostabilizing chromophores to silicone polymers. The photostabilizing chromophores that are covalently bonded to the silicone polymer to form the photostabilizing silicone polymers described herein are compounds of the formula (I):

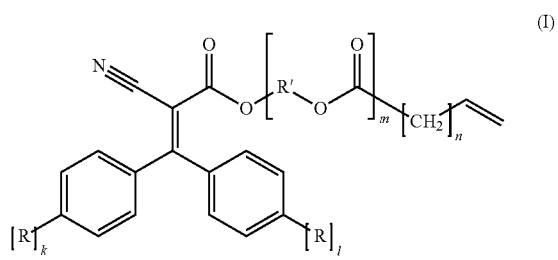

wherein R is a methoxy or an ethoxy group, R' is an organic linker, k, l, m, and n are integers with k and l, are equal to 0 or 1, wherein k and l are not both equal to 1, m is an integer in the range of 1 to about 10, and n is an integer in the range of 2 to about 20. By way of non-limiting examples, the photostabilizing chromophore can have the following specific structures:

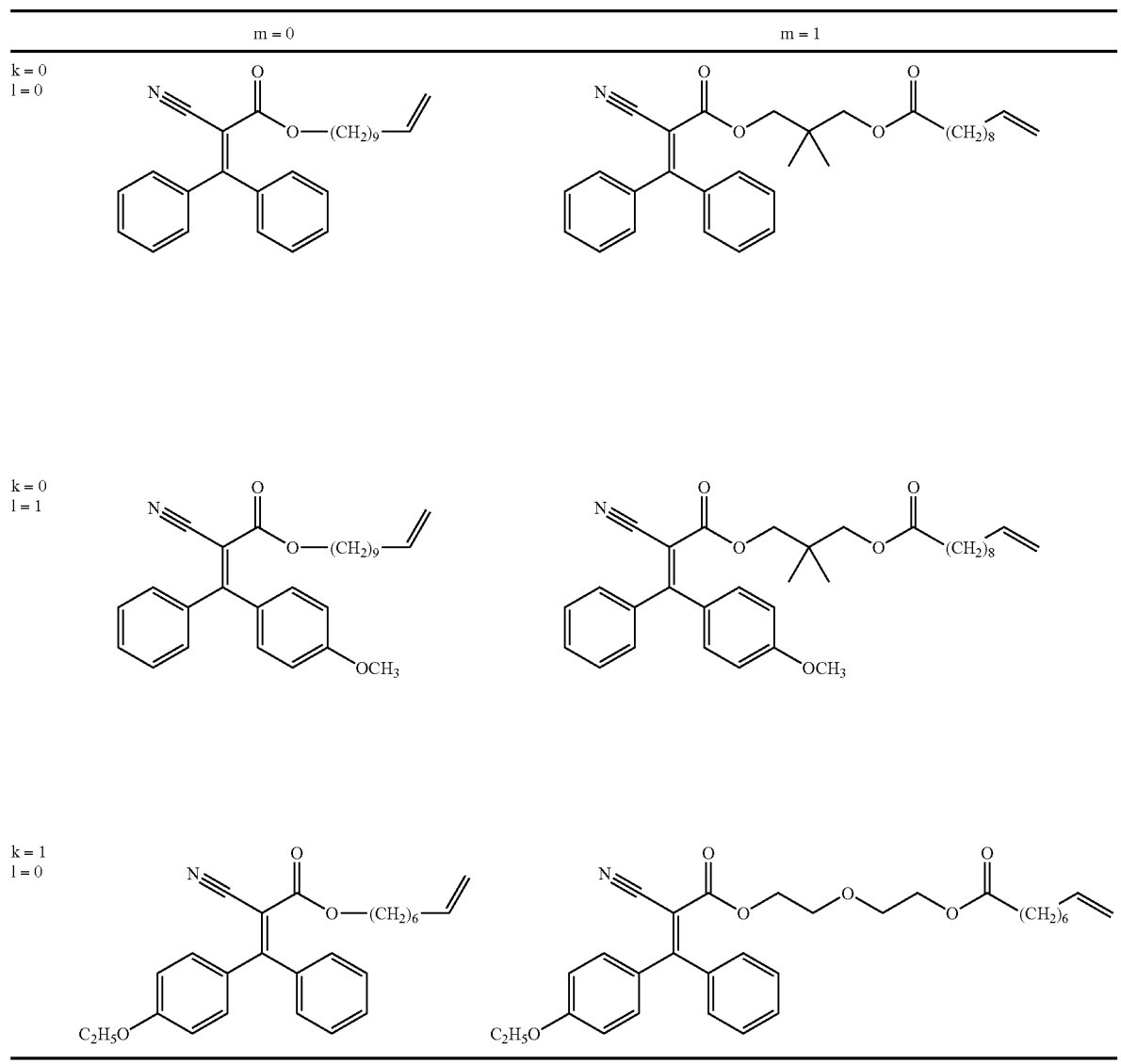

Suitable organic linkers (R') can be, for example, linear, cyclic, and/or branched alkyl chains; alkyl chains containing aromatic groups; aromatic groups; glycolates; dialkylthioethers; dialkylamines; and mixtures thereof. Preferred organic linkers are linear alkyl chains, branched alkyl chains, and glycolates. In particular, organic linkers can be groups having 1 to 20 carbon atoms and assembled individually or from a mixture of the following fragments of $CH_2$, $CH_2CH_2$, $CH_2CH_2CH_2$, $CH_2CH(CH_3)CH_2$, $CH_2C(CH_3)_2CH_2$, $CH_2OCH_2$, $CH_2CH_2OCH_2CH_2$. Non-limiting examples include ethyl ($CH_2CH_2$), ethylene glycolate ($CH_2CH_2OCH_2CH_2$), 2-methylpropyl ($CH_2CH(CH_2)CH_2$), and ethylpropylglycolate ($CH_2CH_2OCH_2CH_2CH_2$). In particular, branched alkyl chains are preferred and one preferred branched alkyl chain is 2,2-dimethylpropyl ($CH_2C(CH_3)_2CH_2$).

Suitable processes for the preparation of photostabilizing chromophores have been described. Briefly, precursors to the photostabilizing chromophore are prepared by reacting substituted benzophenones with ethyl cyanoacrylate through a Knoevengael reaction. An esterification reaction then provides the photostabilizing chromophore of formula (I).

Additionally relevant photostabilizing chromophores include those molecules that contain alternative functional groups for attachment to a silicon atom. For example, the addition of alkyne containing chromophores to silicon has been reported. In particular, various functional groups for attachment to silicon atoms are known to those skilled in the art and are applicable herein provided that the photoprotective and photostabilizing properties of the resulting silicone fluid are not adversely effected.

Herein, the photostabilizing chromophore is attached to a linear or cyclic silicone polymer providing a photostabilizing silicone fluid ("silicone fluid"). The linear silicone polymer can have either of the following general formula (II) or (III):

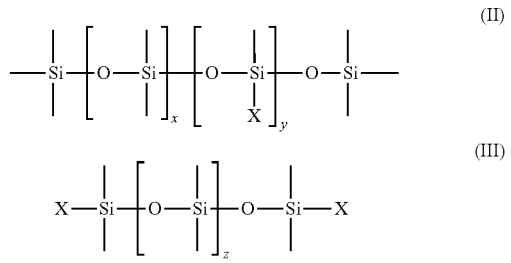

or the silicone polymer can be a linear, random, silicone copolymer. For silicone polymers X designates a reactive functional group that is substituted by or reacted with a photostabilizing chromophore-containing compound for the attachment of the photostabilizing chromophore. The silicone polymers of formula (II) or (III) are linear silicone polymers where x, y and z are integers.

In a first embodiment, where k and l of the chromophore of formula (I) are both equal to zero, the x-integer of silicone fluids of formula (II) can be in the range of 60 to 2000; the y-integer can be in the range of 5 to 100; and the ratio of x/y is at least 10. Preferably, the x-integer is in the range of 60 to 300 and the y-integer is in the range of 6 to 30; more preferably, the x-integer is in the range of 60 to 150; and even more preferably, the x-integer is in the range of 60 to 100. As an example, x is about 60 to about 100, and y is 5 to 10, wherein the ratio of x/y is always at least 10. Preferably, the x/y ratio is about 10/1 to about 15/1. Additionally, while formula (II) depicts a methyl substituted silicone polymer, other substitutions are understood by those of ordinary skill in the art. Suitable Si polymer substituents include $C_1$-$C_{10}$ alkyl, phenyl, and 3,3,3-trifluoropropyl-all can be attached to the Si atoms of the polymer at any position. Moreover, partial substitution of the methyl groups is available and known to those of ordinary skill.

In a second embodiment of the compositions and methods described herein, where k or l of the chromophore of formula (I) is equal to one (R is an alkoxy, preferably methoxy or ethoxy), the x and y integers of silicone fluids of formula (II) are integers of 2 to 2000, same or different, and the ratio of x/y can be any number, preferably 0.5/1 to about 50/1.

The silicone polymers of formula (III) are linear silicone polymers where z is an integer. In the first embodiment described above (no alkoxy in the chromophore group of formula (I) k and l equal 0), the z-integer can be in the range of about 50 to about 1000. Preferably, the z-integer is in the range of 60 to 300; more preferably the z-integer is in the range of 60 to 100. Additionally, while formula (III) depicts a methyl substituted polymer, other substitutions are possible, as understood by those of ordinary skill in the art. Suitable substitutions include $C_1$-$C_{10}$ alkyl, phenyl, and 3,3,3-trifluoropropyl, as well as partial substitution of the methyl groups.

In the second embodiment described above, one R of formula (I) is an alkoxy in the chromophore group, and z can be any integer, preferably 2 to 2000, more preferably 5 to 100.

The linear, random, silicone copolymer of formula IV is a polymer composed of two polymer end caps(E), and at least two different internal groups, designated mer(A) and mer(B):

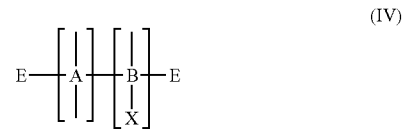

The end caps (E) can be the same or different and, individually, can contain a reactive functional group for the attachment of the photostabilizing chromophore. For example, and similar to formulas II and III, the end caps (E) can be trimethylsilyl groups (—$Si(CH_3)_3$) or dimethylsilyl-functionalized groups (—$Si(CH_3)_2(X)$). Mer(A) preferably has the formula —O—$Si(CH_3)_2$—; mer(B) preferably has the formula —O—$Si(CH_3)(X)$—. Additionally and similar to formulas II and III, the methyl groups on the end caps and the internal groups can be substituted with applicable substitutions, as described above. Moreover, the sum of mer(A) plus mer(B) of the internal groups, e.g., mer(A)+mer(B), wherein one R of the chromophore group of formula (I) is not an alkoxy, is in the range of 60 to about 2000. Preferably, the sum is in the range of 60 to 300, more preferably 60 to about 150, and even more preferably is in the range of 80 to 120. The ratio of mer(A):mer(B) is preferably about 10:1. When one R of the chromophore group of formula (I) is an alkoxy, the sum of mer(A) and mer(B) can be any number preferably 2 to 1000, more preferably 5 to 100.

Dependent on the photostabilizing chromophore and the silicone polymer the method of attaching the photostabilizing chromophore to the silicone polymer varies. When the silicone polymer has hydride (Si—H) functional groups a standard hydrosylation reaction can be employed. Moreover, a hydrosylation reaction can be carried out with photostabilizing chromophores that contain alkenyl and alkynyl functionalities, examples of alkenyl containing photostabilizing chromophores are depicted above and often correspond to formula (I). Other methods of attaching the photostabilizing chromophore to the silicone polymer will be apparent to one of ordinary skill in the art.

To achieve the full advantage of the compositions and methods described herein, the above described silicone fluids are combined with one or more photodegradable photoabsorbing compounds so that the silicone polymer photostabilizes the photodegradable compounds. Additionally, the silicone fluids can be combined with dermatologically acceptable materials, e.g. sunscreens, to impart photostabilization or enhance or improve photoprotection. For example, silicone fluids, materials containing silicone fluids, and other materials can be combined to provide photostabilized plastic, glass, cream, lotion, gel, non-viscous liquid, and/or viscous liquid compositions.

Preferably, the silicone fluids are combined with cosmetically acceptable materials. These cosmetically acceptable materials include emollients, stabilizers, emulsifiers, thickeners, humectants, surfactants, preservatives, vitamins, anti-foaming agents, fragrances, anti-irritants, other organomodified silicones, chelators, opacifiers, polar oils, nonpolar oils, waxes, alcohols, polyols, propellants, colorants, and pigments.

Additionally, preferable compositions include those where silicone fluid is combined with one or more dibenzoylmethane derivative. Dibenzoylmethane derivatives include 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; and 2,6-dimethyl-4-tert-butyl-4'-methoxydibenzoylmethane.

Additional compositions include those where the silicon fluid is combined with other photoactive compounds. Examples of photoactive compounds are p-aminobenzoic acid and salts and derivatives thereof; anthranilate and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; naphthalene dicarboxylic acids, derivatives, dimers, oligimers, polymers, and salts and combinations thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof.

As will be appreciated by persons of ordinary skill in the art, dermatocosmetic compositions comprising silicone fluids may also contain one or more film-forming polymers, rheology-modifying agents, plasticizers, structuring agents, viscosity modifiers, thickener, gellants, surfactants, anti-aging ingredients (e.g., ingredients that help to reduce the appearance of fine lines and wrinkles caused by environmental or intrinsic aging, including botanical extracts, short-chain peptides), moisturizers and/or humectants, self-tanning agents (e.g., dihydroxyacetone), and vitamins and/or vitamin derivatives. These ingredients are listed in the International Cosmetic Ingredient Dictionary and Handbook, (11th Edition), published by the Cosmetics Fragrance and Toiletries Association, as well as in U.S. Pat. Nos. 6,492,326 and 6,277,892 and US Patent Application Publication Nos. 2004/0180020 and 2005/0142095.

Surprisingly, the additional of the silicone fluid to photoprotective materials or materials containing photoprotective compounds enhanced the photostability of the material and/or compounds. Importantly, the added photostability decreased the amount of photoprotective compounds necessary to fully protect the material or its wearer from UV radiation.

EXAMPLES

The following examples are provided to illustrate the invention, but are not intended to limit the scope thereof.

One general method for preparing photoprotective chromophores can be understood from the specific procedures outlined below. In a large flask are combined 4-ethoxy benzophenone and ethyl cyanoacetate in a ratio of 1:1.35. The materials are then dissolved in a 5:1 mixture of toluene and acetic acid; followed by the addition of 0.1 mole equivalence of an ammonium acetate catalyst. The mixture is heated and any water formed during the reaction is distilled from the reaction mixture. Then the reaction mixture is cooled to room temperature and ethyl acetate is added to dissolve the solids and the mixture is washed with water. Then solvents are removed by distillation. The final solid product is re-crystallized from either hot methanol or a toluene/methanol mixture. The overall reaction is summarized as follows:

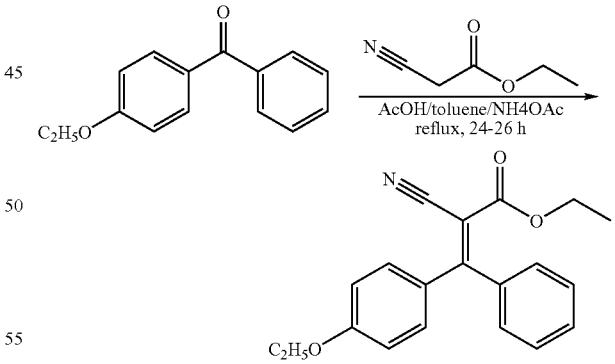

The ethyl α-cyano-β,β-diphenylacrylate can then be converted into a photostabilizing chromophore of formula (I) by treating it with 10-undecen-1-ol in the presence of a catalyst, e.g., monobutyl tin dihydroxychloride $(C_4H_9)Sn(OH)_2Cl$. The reactants and catalyst are heated at a temperature of about 150° C. to about 200° C., preferably from about 180° C. to about 190° C., for five to six hours. Then excess 10-undecen-1-ol is removed under vacuum and a mixture of silica gel, aluminum oxide, magnesium oxide and potassium oxide is added. The product is then obtained by filtration. It has been observed that the products from this reaction are remarkably pure, e.g. analysis has shown one such product to be 99.81% pure, and have very low moisture content, about 0.028%, and a Gardner scale color of 3.5.

An alternative photostabilizing chromophore of formula (I) can be made by first treating, for example, ethyl α-cyano-β,β-diphenylacrylate with 2,2-dimethyl-1,3-propanediol (neopentyl glycol). Here, a five-fold excess of neopentyl glycol is combined with the ethyl α-cyano-β,β-diphenylacrylate and a catalytic amount of sodium carbonate. The mixture is heated and ethanol generated by the reaction is removed by distillation. When the reaction is completed, toluene is added and the sodium carbonate is filtered off while the solution is still hot. The product solution is washed several times with water and then the solution is concentrated to afford crystallization of a product. This product can then be treated with 10-undecenoic acid, and methanesulphonic acid in toluene; heated and any water formed during the reaction is distilled from the mixture. This product mixture is then washed twice with a solution of NaCl in water. The product is then filtered and dried. The final photostabilizing chromophore made by the above procedure is greater than 99% pure and does not require further purification. The overall reaction described above is summarized as follows:

Unexpectedly, it was observed that the silicone fluids of the present invention have a synergistic photostabilizing effect when combined with secondary photostabilizing materials, e.g., octocrylene, in sunscreening formulations. The synergistic effect was observed by measuring the loss of UVA, UVB and SPF protection for formulations (A) having a mixture of a silicone fluid and octocrylene, (B) having of octocrylene but no silicone fluid, (C) having silicone fluid and no octocrylene, and (D) having neither silicone fluid nor octocrylene. Illustrative comparative measurements on these sunscreen emulsion formulations before and after irradiation with the equivalent of 35 MED of midday sun on a mid-summer day (more particularly, noon sun on July 3rd in Albuquerque, N. Mex.) are shown below and in the drawing.

|  | Formulation Example A | Formulation Example B | Formulation Example C | Formulation Example D |
|---|---|---|---|---|
| Avobenzone | 3.00% | 3.00% | 3.00% | 3.00% |
| Octisalate | 5.00% | 5.00% | 5.00% | 5.00% |
| Homosalate | 7.50% | 7.50% | 7.50% | 7.50% |
| Benzophenone- | 0.49% | 0.49% | 0.49% | 0.49% |

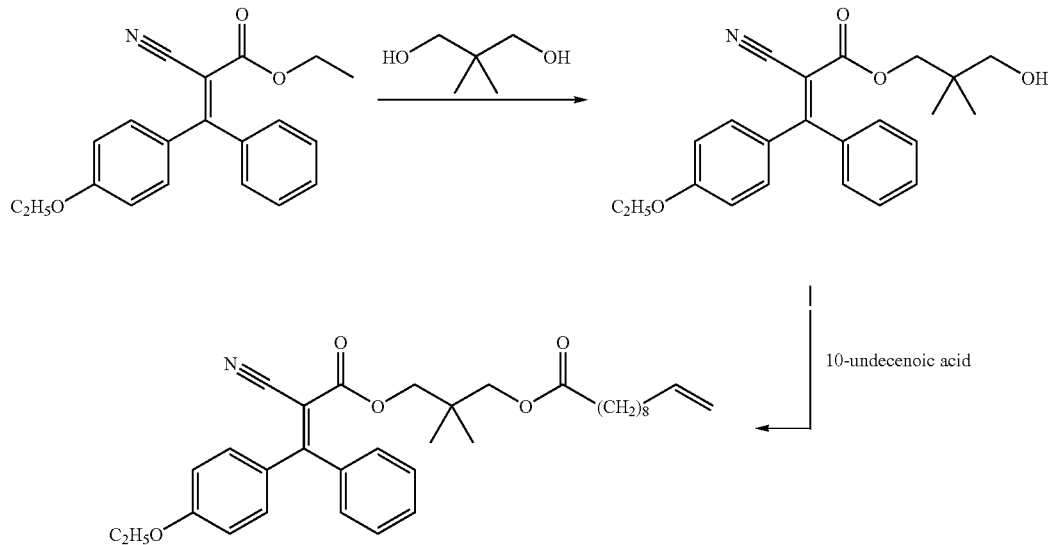

A standard hydrosilylation reaction can be used to make the silicone fluids of the present invention. This type of reaction is known to persons of ordinary skill in the art and is described, generally, in U.S. Pat. No. 6,841,649 (to O'Lenick Jr.) the disclosure of which is incorporated herein by reference in its entirety.

A general hydrosilation procedure involves combining a photostabilizing chromophore of formula (I) and a silicone polymer containing a hydride functionality, often in a solvent—typically isododecane or cyclopentasiloxane. The temperature of the mixture is then increased to about 50° C. and a Karnstedt catalyst is added. (Karnstedt catalyst is an article of commerce known to persons of ordinary skill in the art and described in U.S. Pat. No. 3,715,334.) The reaction is run until completion and then sodium bicarbonate is added. The product is then filtered through a 4-micron pad. When a solvent is used the product can remain in the solvent or the solvent can be removed by vacuum distillation.

-continued

|  | Formulation Example A | Formulation Example B | Formulation Example C | Formulation Example D |
|---|---|---|---|---|
| 3 |  |  |  |  |
| Octocrylene | 2.75% | 2.75% | 0.00% | 0.00% |
| Silicone Fluid | 3.00% | 0.00% | 5.75% | 0.00% |
| Phenylethyl benzoate | 0.00% | 0.00% | 0.00% | 2.75% |
| Dimethicone (350 cSt) | 0.00% | 1.25% | 0.00% | 1.25% |
| Methyl trimethicone | 0.00% | 1.75% | 0.00% | 1.75% |
| VP/Eicosene copolymer | 1.00% | 1.00% | 1.00% | 1.00% |
| Cetearyl alcohol | 0.36% | 0.36% | 0.36% | 0.36% |
| Steareth-21 | 0.80% | 0.80% | 0.80% | 0.80% |
| Steareth-2 | 0.60% | 0.60% | 0.60% | 0.60% |
| Potassium cetyl | 3.00% | 3.00% | 3.00% | 3.00% |

| | Formulation Example A | Formulation Example B | Formulation Example C | Formulation Example D |
|---|---|---|---|---|
| phosphate & Hydrogenated palm glycerides | | | | |
| Disodium EDTA | 0.10% | 0.10% | 0.10% | 0.10% |
| Glycerin | 4.00% | 4.00% | 4.00% | 4.00% |
| Benzyl alcohol | 1.00% | 1.00% | 1.00% | 1.00% |
| Methylparaben | 0.10% | 0.10% | 0.10% | 0.10% |
| Propylparaben | 0.05% | 0.05% | 0.05% | 0.05% |
| Water | 62.25% | 62.25% | 62.25% | 62.25% |
| Acrylamide/ Sodium acryloyldimethyl taurate copolymer | 2.50% | 2.50% | 2.50% | 2.50% |
| Aluminum starch octenyl succinate | 2.50% | 2.50% | 2.50% | 2.50% |
| Loss of UVA protection | −2.62% | −10.01% | −30.36% | −63.77% |
| Loss of UVB protection | −0.38% | −6.42% | −11.74% | −11.16% |
| Loss of SPF | −2.17% | −9.65% | −18.16% | −21.82% |

Formulation Examples A-D were each made according to the following general procedure of mixing together Avobenzone, Octisalate, Homosalate, Benzophenone-3, Octocrylene, Silicone Fluid, and Phenylethyl benzoate and heating to 90° C. Then VP/Eicosene copolymer, Cetearyl alcohol, Steareth-21, Steareth-2, Potassium cetyl phosphate & Hydrogenated palm glycerides are added sequentially. In a different vessel disodium EDTA and Glycerin are added to the water and the solution warmed to 90° C. The first mixture is then added to the water mixture and stirred vigorously until the temperature is below 55° C. When cool, a mixture of Benzyl alcohol, Methylparaben, and Propylparaben is added to the earlier mixture. Acrylamide/Sodium acryloyldimethyl taurate copolymer is then added followed by Aluminum starch octenyl succinate. Finally, Dimethicone (350 cSt) and Methyl trimethicone are added and the mixture mixed until uniform.

The foregoing description is given for clearness of understanding only, and no unnecessary limitations should be understood therefrom, as modifications within the scope of the invention may be apparent to those having ordinary skill in the art.

What is claimed is:

1. A method of photostabilizing a photodegradable UV-absorbing compound or polymer comprising
adding a photostabilizing amount of a silicone fluid to the photodegradable compound or polymer,
wherein the silicone fluid has a formula (2):

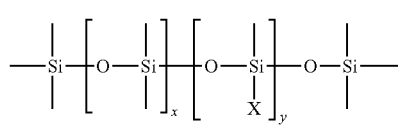

(2)

wherein x is an integer in the range of 60 to 150; y is an integer in the range of 6 to 30; a ratio x:y is in a range of about 10:1 to about 20:1; and X is a photostabilizing chromophore of formula (3):

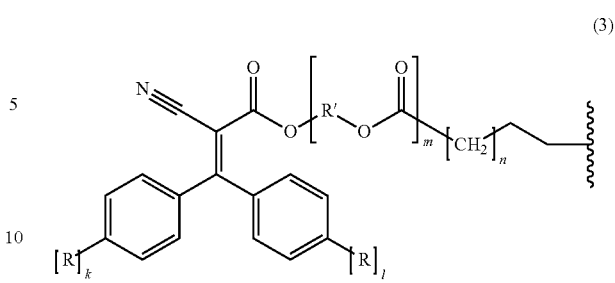

(3)

wherein k and l equal zero or one of k and l equals 1 and the other is zero; R is an alkoxide; R' is an organic linker; m is an integer in a range of zero to about ten; and n is an integer in a range from two to about twenty.

2. A method of photostabilizing a photodegradable UV-absorbing compound or polymer comprising
adding a photostabilizing amount of a silicone fluid to the photodegradable compound or polymer, wherein the silicone fluid comprises a photostabilizing-chromophore-substituted linear, random copolymer of formula IV:

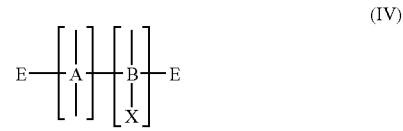

(IV)

wherein the random copolymer comprises end caps (E), multiple mer(A) units, and multiple mer(B) units; wherein the end caps (E) are independently selected from the group consisting of —Si(CH$_3$)$_3$ and —Si(CH$_3$)$_2$(X); the mer(A) units are —OSi(CH$_2$)$_2$—; the mer(B) units are —OSi(CH$_2$)(X)—; a ratio of the number of units of mer(A):mer(B) is at least 10:1, a sum of the number of mer(A) units and mer(B) units is in the range of 80 to 300; and X is a photostabilizing chromophore of a formula (6):

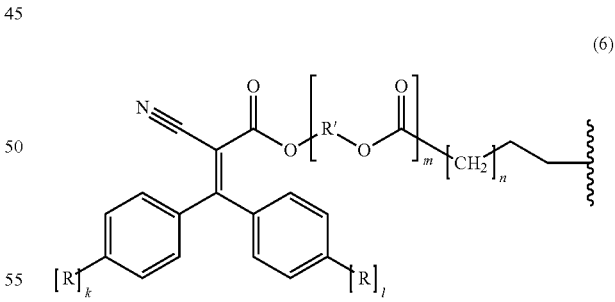

(6)

wherein R is selected from the croup consisting of methoxy and ethoxy; R' is an organic linker; k and l equal zero or one of k and l equals 1 and the other is zero; m is an integer in a range of zero to about ten; and n is an integer in a range of 2 to about 20.

3. The method of claim 2, wherein the sum of the number of units of mer(A) and mer(B) is in the range of 80 to 150.

4. The method of claim 3, wherein the sum of the number of units of mer(A) and mer(B) is in the range of 80 to 120.

5. The method of claim 2, wherein m is equal to one and the organic linker is selected from the group consisting of $CH_2$, $CH_2CH_2$, $CH_2CH_2CH_2$, $CH_2CH(CH_3)CH_2$, $CH_2C(CH_3)_2CH_2$, $CH_2OCH_2$, $CH_2CH_2OCH_2CH_2$, and mixtures thereof.

6. The method of claim 5, wherein the organic linker is $CH_2C(CH_3)_2CH_2$.

7. The method of claim 2, wherein the photodegradable compound comprises a dibenzoylmethane derivative.

8. The method of claim 7, wherein said dibenzoylmethane derivative is selected from the group consisting of 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

9. The method of claim 2 wherein the photodegradable compound comprises a photoactive compound selected from the group consisting of p-aminobenzoic acid and salts and derivatives thereof; anthranilate and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; naphthalene dicarboxylic acids, derivatives, dimers, oligimers, polymers, and salts and combinations thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations thereof.

10. The method of claim 1, wherein the ratio x:y is about 10:1.

11. The method of claim 1, wherein x is an integer in the range of 60 to about 100.

12. The method of claim 11, wherein x is about 60.

13. The method of claim 11, wherein x is about 80.

14. The method of claim 11, wherein x is about 100.

15. The method of claim 1, wherein m is equal to one and the organic linker is selected from the group consisting of $CH_2$, $CH_2CH_2$, $CH_2CH_2CH_2$, $CH_2CH(CH_3)CH_2$, $CH_2C(CH_3)_2CH_2$, $CH_2OCH_2$, $CH_2CH_2OCH_2CH_2$, and mixtures thereof.

16. The method of claim 15, wherein the organic linker is $CH_2C(CH_3)_2CH_2$.

17. The method of claim 1, wherein the photodegradable UV-absorbing compound comprises a dibenzoylmethane derivative.

18. The method of claim 17, wherein said dibenzoylmethane derivative is selected from the group consisting of 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

19. The method of claim 1, wherein the photodegradable UV-absorbing compound comprises a photoactive compound selected from the group consisting of p-aminobenzoic acid and salts and derivatives thereof; anthranilate and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; naphthalene dicarboxylic acids, derivatives, dimers, oligimers, polymers, and salts and combinations thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations thereof.

20. A method of photostabilizing a photodegradable UV-absorbing compound or polymer comprising
adding a photostabilizing amount of a silicone fluid to the photodegradable compound or polymer,
wherein the silicone fluid has a formula (2):

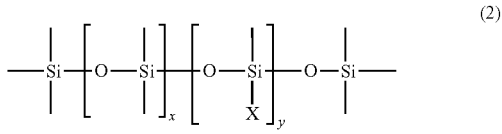

(2)

wherein x is about 100; a ratio x:y is in a range of about 10:1 to about 15:1; and X is a photostabilizing chromophore of formula (3):

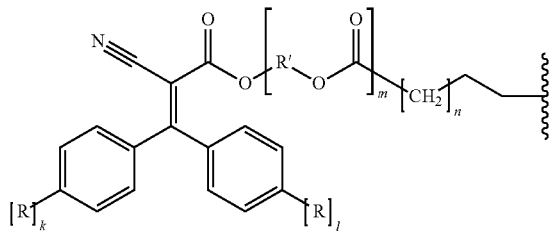

(3)

wherein k and l equal zero or one of k and l equals 1 and the other is zero; R is a methoxyl or an ethoxy group; R' is an organic linker selected from the group consisting of $CH_2$, $CH_2CH_2$, $CH_2CH_2CH_2$, $CH_2CH(CH_3)CH_2$, $CH_2C(CH_3)_2CH_2$, $CH_2OCH_2$, $CH_2CH_2OCH_2CH_2$, and mixtures thereof; m is an integer in a range of zero to about ten; and n is an integer in a range from two to about twenty.

21. The method of claim 1, further including the step of adding a second photostabilizer to the photodegradable UV-absorbing compound or polymer.

22. The method of claim 21, wherein the second photostabilizer is octocrylene to provide photostabilizing synergism.

* * * * *